US006905468B2

(12) United States Patent
McMorrow et al.

(10) Patent No.: US 6,905,468 B2
(45) Date of Patent: Jun. 14, 2005

(54) THREE-DIMENSIONAL SYSTEM FOR ABDOMINAL AORTIC ANEURYSM EVALUATION

(75) Inventors: Gerald J. McMorrow, Duvall, WA (US); Jongtae Yuk, Redmond, WA (US); William Barnard, Woodinville, WA (US)

(73) Assignee: Diagnostic Ultrasound Corporation, Bothell, WA (US)

( * ) Notice: Subject to any disclaimer, the term of this patent is extended or adjusted under 35 U.S.C. 154(b) by 293 days.

(21) Appl. No.: 10/246,945

(22) Filed: Sep. 18, 2002

(65) Prior Publication Data

US 2004/0054280 A1 Mar. 18, 2004

(51) Int. Cl.[7] .................................................. A61B 8/00
(52) U.S. Cl. ........................................ 600/443; 128/916
(58) Field of Search ................................ 600/443, 447, 600/450, 466–467; 128/916

(56) References Cited

U.S. PATENT DOCUMENTS

| | | | | |
|---|---|---|---|---|
| 5,125,410 A | * | 6/1992 | Misono et al. ............... | 600/463 |
| 5,159,931 A | * | 11/1992 | Pini ............................ | 600/443 |
| 5,487,388 A | * | 1/1996 | Rello et al. .................. | 600/445 |
| 5,972,023 A | * | 10/1999 | Tanner et al. ............... | 606/219 |
| 6,148,095 A | * | 11/2000 | Prause et al. ............... | 382/131 |
| 6,151,404 A | * | 11/2000 | Pieper ......................... | 382/128 |
| 6,511,325 B1 | * | 1/2003 | Lalka et al. ................. | 434/272 |
| 6,524,249 B2 | * | 2/2003 | Moehring et al. ........... | 600/438 |
| 6,643,533 B2 | * | 11/2003 | Knoplioch et al. .......... | 600/407 |
| 6,716,175 B2 | * | 4/2004 | Geiser et al. ................ | 600/450 |
| 2001/0031920 A1 | * | 10/2001 | Kaufman et al. ............ | 600/431 |

OTHER PUBLICATIONS

Santilli, J.D. et al , Diagnosis and Treatment of Abdominal Aortic Aneurysms, Amer. Family Physician V.56 No. 4, Sep. 15, 1997.*

* cited by examiner

Primary Examiner—Francis J. Jaworski
(74) Attorney, Agent, or Firm—Jensen & Puntigam, P.S.

(57) ABSTRACT

A data collection device obtains three-dimensional ultrasound scan information of a portion of the abdominal aorta. A plurality of transducer elements are arranged to provide overlapping coverage. The data collection device is first positioned over the aorta by an operator; a one-dimensional scan with a Doppler sound generator operating on the blood flow is used to verify proper initial positioning of the device. Three-dimensional scan information is then obtained and converted from plane coordinates into spherical coordinates such that the resulting converted scan line planes are perpendicular to the aorta. The information in each converted scan line plane is then processed to determine the boundaries of the aorta, from which diameter information is then calculated. Diameter measurements over a given region of the aorta can be used to determine and monitor an aneurysm in the aorta.

16 Claims, 6 Drawing Sheets

THREE-DIMENSIONAL SYSTEM FOR ABDOMINAL AORTIC ANEURYSM EVALUATION

TECHNICAL FIELD

This invention relates generally to a system for ultrasound imaging of the descending abdominal aorta artery, and more specifically concerns such a system in which the ultrasound data is acquired and analyzed without the aid of a skilled sonographer.

BACKGROUND OF THE INVENTION

The aorta artery in the abdomen carries blood from the heart to the abdominal region. One disorder of the abdominal aorta is known as an abdominal aortic aneurysm, which is a permanent localized dilation of the arterial wall of the abdominal aorta. When dilation of the arterial wall is greater than 1.5 times the typical, i.e. nominal, diameter, it is referred to as an aneurysm. A normal abdominal aorta is shown in FIG. 1. FIG. 1A shows a typical aortic aneurysm at 16. An aortic aneurysm is usually located below the renal arteries 18 and the kidney arteries 20 and above the aorta-iliac bifurcation 22. Below the aortic-iliac bifurcation 22 are additional arteries. Abdominal aortic aneurysms are a fairly common disorder, occurring in approximately 5–7% of the population over age 60. Abdominal aortic aneurysms, depending upon their size, result in pressure on adjacent tissue structure and organs, causing potential embolization and/or thrombosis in those tissues/organs. Rupture of the aneurysm typically results in death, and comprises approximately 2% of all deaths in men over 60 years of age.

Accurate diagnosis of an abdominal aortic aneurysm is important in preventing rupture, as well as in controlling the expansion of the aneurysm. Convention two-dimension B-mode ultrasound scan devices are currently used to produce measurements of aortic aneurysms, both axially (longitudinally) along the aorta and laterally (radially) across the aorta. Typically, the accuracy is within three millimeters of the actual size of the aneurysm, using conventional CT or MRI processing. These conventional systems, whoever, are very expensive, both to purchase/lease and to maintain. Further, a trained sonographer is necessary to interpret the results of the scans. This results in many aneurysms going undetected and/or being not consistently monitored after discovery, until rupture and resulting death of the patient.

Hence, it would be desirable to have a low-cost yet accurate system to detect and measure abdominal aortic aneurysms. In particular, it would be useful to a primary care physician or emergency personnel to have a low-cost device which provides accurate information concerning aortic aneurysms, without the necessity of a trained technician to interpret the scan results.

SUMMARY OF THE INVENTION

Accordingly, the present invention is a system and corresponding method for abdominal aortic aneurysm evaluation and monitoring, which comprises a data collection device/method step for obtaining three-dimensional ultrasound scan information of a selected portion of an abdominal aorta, in the form of a plurality of scan line planes; a processor/step for converting the scan line plane information into coordinates in which the converted scan line planes slice approximately perpendicularly through the aorta; a processor/step for determining aorta boundary information from the converted scan information; and a calculation circuit/step for calculating the diameter of the aorta from the boundary information, wherein diameter information from the aorta at a plurality of locations therealong is useful in determining the existence of an aneurysm in the abdominal aorta artery.

Another aspect of the invention is a system for abdominal aortic aneurysm monitoring, comprising: an apparatus for obtaining three-dimensional ultrasound information for a selected portion of an abdominal aorta and for processing said ultrasound information to determine aorta boundaries; and a processor for compounding the boundary information to produce a visual representation of the aorta, surface-rendered to produce a realistic representation of the aorta.

BEST MODE FOR CARRYING OUT THE INVENTION

As briefly discussed above, an abdominal aortic aneurysm is defined as a dilation of the wall of the abdominal aorta. The average aorta diameter is two centimeters (somewhat greater in men and somewhat less in women). Since the definition of an aneurysm is 1.5 times the average aortic diameter, an aorta diameter greater than three centimeters is an indication of an aneurysm. Aneurysm diameters of between three centimeters and five centimeters should be monitored regularly, while an aneurysm greater than five centimeters in diameter should have prompt surgical treatment to prevent rupture and resulting probable death.

In the present invention, generally, a conventional ultrasound transducer, which in operation transmits and receives back an ultrasound beam, is positioned by an operator on a patient approximately over the abdominal aorta. This is explained in more detail below. The device first produces an ultrasound signal which is processed by Doppler techniques relative to the blood flow through the artery to produce an audible sound based on blood flow. The operator uses the Doppler sound to accurately position the device relative to the aorta.

The device is then operated to produce a three-dimensional scan by generating a plurality of individual scan lines at successive angles of rotation. The resulting three-dimensional scan will encompass the descending aorta. This operation of the ultrasound transducer device can be readily carried out by emergency personnel; a trained sonographer or ultrasound technician is not necessary. The resulting data can then be processed, either locally or remotely, to produce an indication of the existence of an aneurysm and the extent of the aneurysm. In selected cases, an actual image of the aneurysm can be displayed for evaluation by a trained sonographer. However, this is typically not necessary with the present invention, i.e. numerical information over a selected portion of the aorta is sufficient.

Figure 1A:
FIGS. 1 and 1A are simplified drawings showing the aortic artery, without and with an aortic aneurysm.
Figure 1:
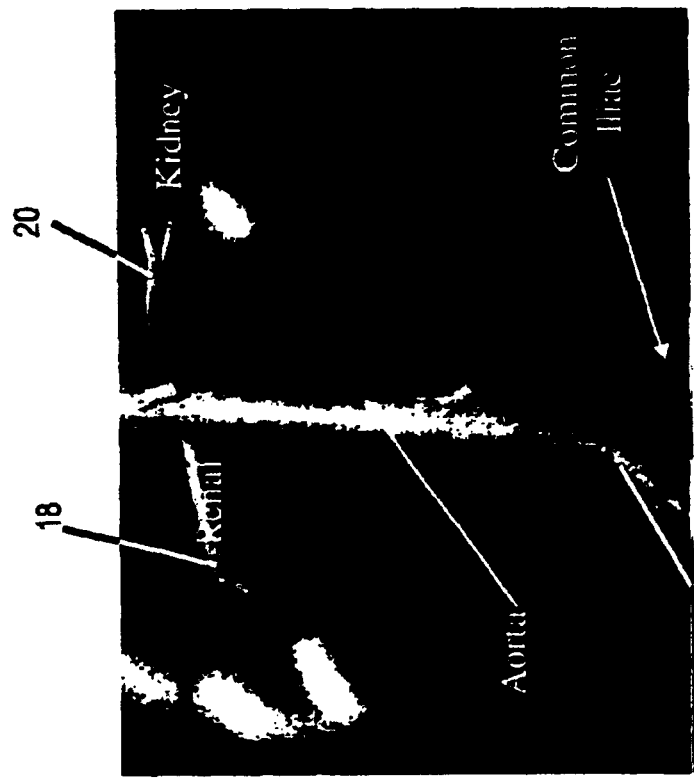
Figure 2:
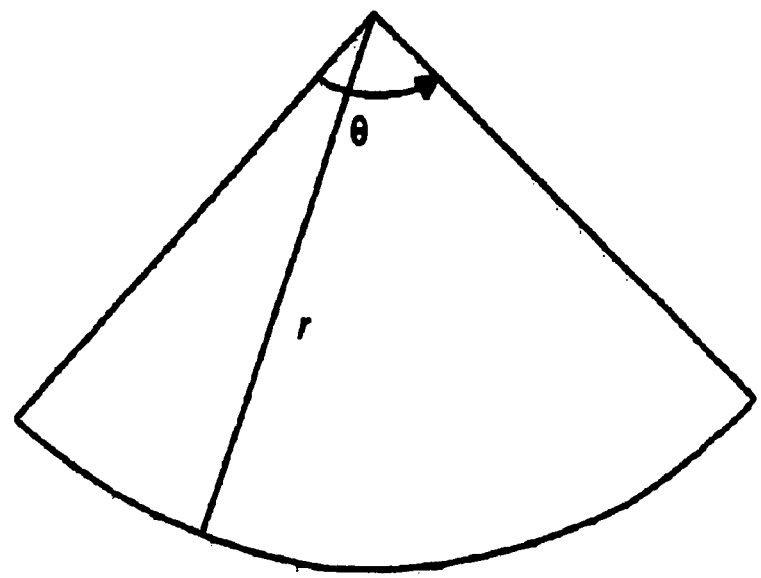
FIGS. 2 and 2A are diagrams showing a 3-D scan using ultrasound with plane coordinates.
Figure 2A:
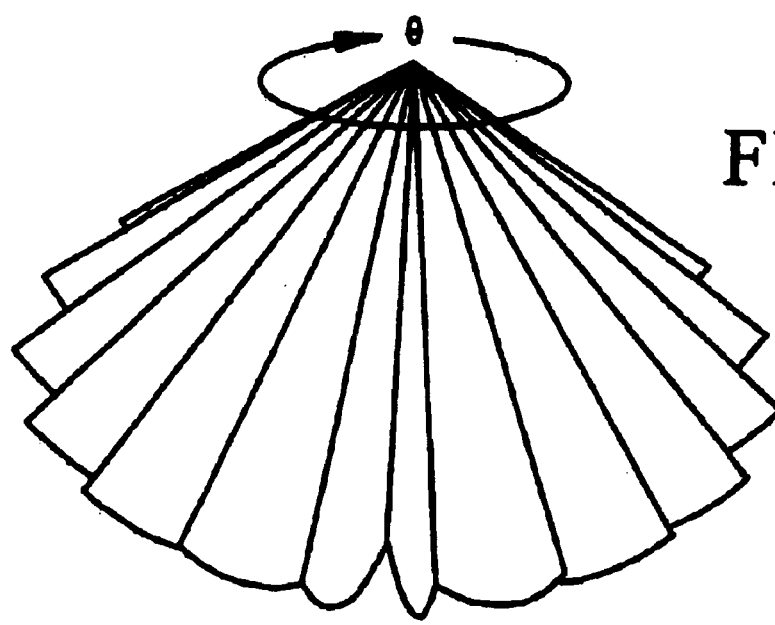

Referring now to FIGS. 2 and 2A, an ultrasound beam is generated and transmitted in conventional fashion by one or more ultrasound transducers in a hand-held scanner apparatus. In the embodiment shown, each transducer operates at a frequency of 3.7 MHz, producing a beam 30 approximately 15 centimeters deep and 0.04 radians wide. Each transducer includes a motor, which tilts the transducer through a 120° angle (Ø) by moving the transducer first 60° clockwise and then 60° counter-clockwise. The depth of the beam is indicated by the designation r. This produces a two-dimensional single sector (plane) image of selected depth. A second motor then rotates the transducer in the embodiment shown approximately 15° (angle θ), and another 120° scan plane image is produced, by action of the first motor. This process is repeated until the transducer is rotated in the angle θ dimension to 180°, resulting in a cone-shaped, three-dimensional image data set comprising 12 individual planes or sectors of data of a selected known depth.

FIG. 2 shows a single plane or sector of radius r and angle Ø 120°, while FIG. 2A shows 12 planes of data arranged to give a three-dimensional cone-shaped coverage, with each plane/sector separated in angle θ by 15°. In this arrangement, the range r (depth) for a scan, the scan or tilt angle Ø and the rotation angle θ completely identifies each point in the three-dimensional data set. These are generally referred to as plane coordinates.

One important aspect of the present invention is the initial positioning, i.e. aiming, of the scanner prior to the full capture of the data needed to produce the abdominal diagnosis. The scan signals at this point are in a single dimension, with rotational angle θ being zero. The transducer is positioned at an angle over the aorta such that the resulting one-dimensional scan line will intersect the body at an angle of 25°, although this can be varied to some extent, so that the flow of blood through the aorta will have an advancing component of its velocity vector relative to the transducer. This will cause the Doppler backscatter to be shifted to the upper side band of the transmitted signal spectrum. The resulting audio Doppler signal is provided through a speaker in the scanner. The scanner is moved around by the operator to the point where the maximum sound is heard, indicating the point of maximum blood flow. The scanner is then considered to be centered on the aorta. This arrangement makes the initial positioning, i.e. aiming, of the scanner simple and straightforward, without requiring trained personnel.

Hence, the data collection device, i.e. scanner, can be properly positioned on the patient without the necessity of an image, i.e. it is a "blind" positioning. When the audible sounds of blood flow are heard, the operator initiates the regular capture mode of the scanner by depressing a scan button on the device. The instrument then "captures" a three-dimensional scan cone with B-mode image data covering a portion of the aorta. In the present embodiment, the scan data is interpreted by algorithms to produce information concerning the aorta walls, which permits the determination of aortic diameter, for instance.

One cone-shaped, three-dimensional scan typically will not cover the entire abdominal aorta to include the renal artery, the iliac bifurcation and the superior mesenteric artery. Several approaches are used to cover the large field of view.

Figure 3:
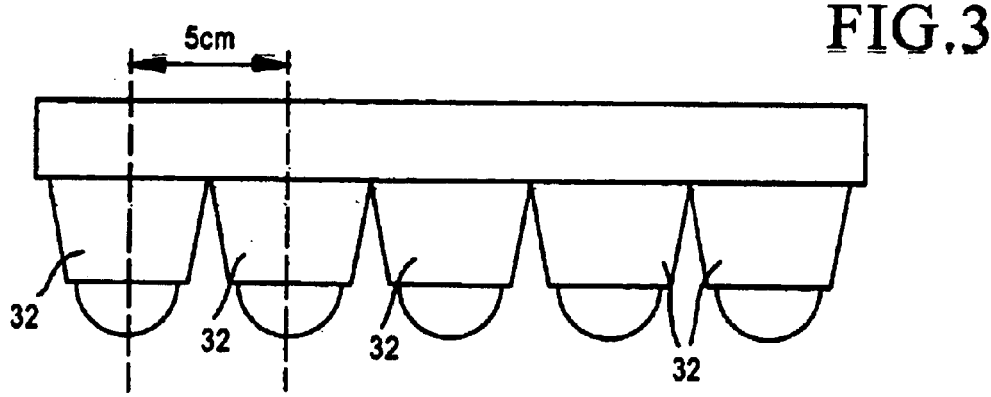
FIG. 3 is a drawing showing the arrangement of five scanheads for adequate coverage of the abdominal aorta area.

In one embodiment, five individual transducers 32—32 are arranged linearly, with a physical separation between the scanheads, as shown in FIG. 3. In this case, the separation is five centimeters, although this can be varied. Typically, the five scanhead arrangement will cover the abdominal region to provide scan coverage of the desired portion of the aorta. In this embodiment, ultrasound signals are generated in parallel with an identical motion in such a way that they do not interfere with each other. Since the geometry of the plurality of scan cones is fixed, this embodiment has the best cone-to-cone coordination. This is the fastest system but also the most hardware-intensive and expensive. The resulting data can be sent by the internet for remote processing.

Other arrangements and numbers of transducers can, however, be used. The geometry of movement of the transducers in the scanner can be arranged to reduce the computational requirements of the system. For instance, the individual transducers can be sequentially energized so that the information from only one scanhead at a time is being processed. The resulting information can then be combined to produce comprehensive scan information concerning the abdominal aorta.

In one such additional arrangement, multiple scans using a single ultrasound scan cone are made. The user takes multiple single cone scans of the aorta area, repositioning the instrument each time along a straight line down the patient's abdomen. The data for all the scans is stored and then sent via the internet for remote processing.

In still another embodiment, using a single scan cone and a single scan, the aortic diameter is displayed on the instrument following a scan. The user moves the instrument around on the abdomen to find the largest diameter, which is calculated either from a full three-dimensional scan cone or a single two-dimensional power Doppler plane.

If a single two-dimensional power Doppler plane is used, the diameter information is presented faster, the user looks for the maximum aorta diameter, and when that is determined, pushes a button, which results in the device taking a full three-dimensional scan. The three-dimensional scan produces a more accurate maximum diameter, and the resulting three-dimensional image is stored for later upload to the web server. In this approach, however, the user must orient the instrument such that the two-dimensional plane cuts across a true cross-section of the aorta. The Doppler audio aiming feature is not utilized, since power Doppler includes this same information.

The use of a three-dimensional scan cone removes this orientation requirement, permitting the user to position the device in any orientation. The user simply takes several three-dimensional image scans, moving along the patient's abdomen. When not doing a full three-dimensional image, the device outputs Doppler-audio to guide the user aiming the device. After each scan, the diameter of the section of the aorta covered by that scan is displayed and the image is stored if the diameter from the new scan is larger than any previous diameter. The image produced in this embodiment, whether it be from two-dimensional power Doppler plane or three-dimensional scan cone, can be optimally transmitted via the internet for remote enhanced processing and rendering.

Figure 6:
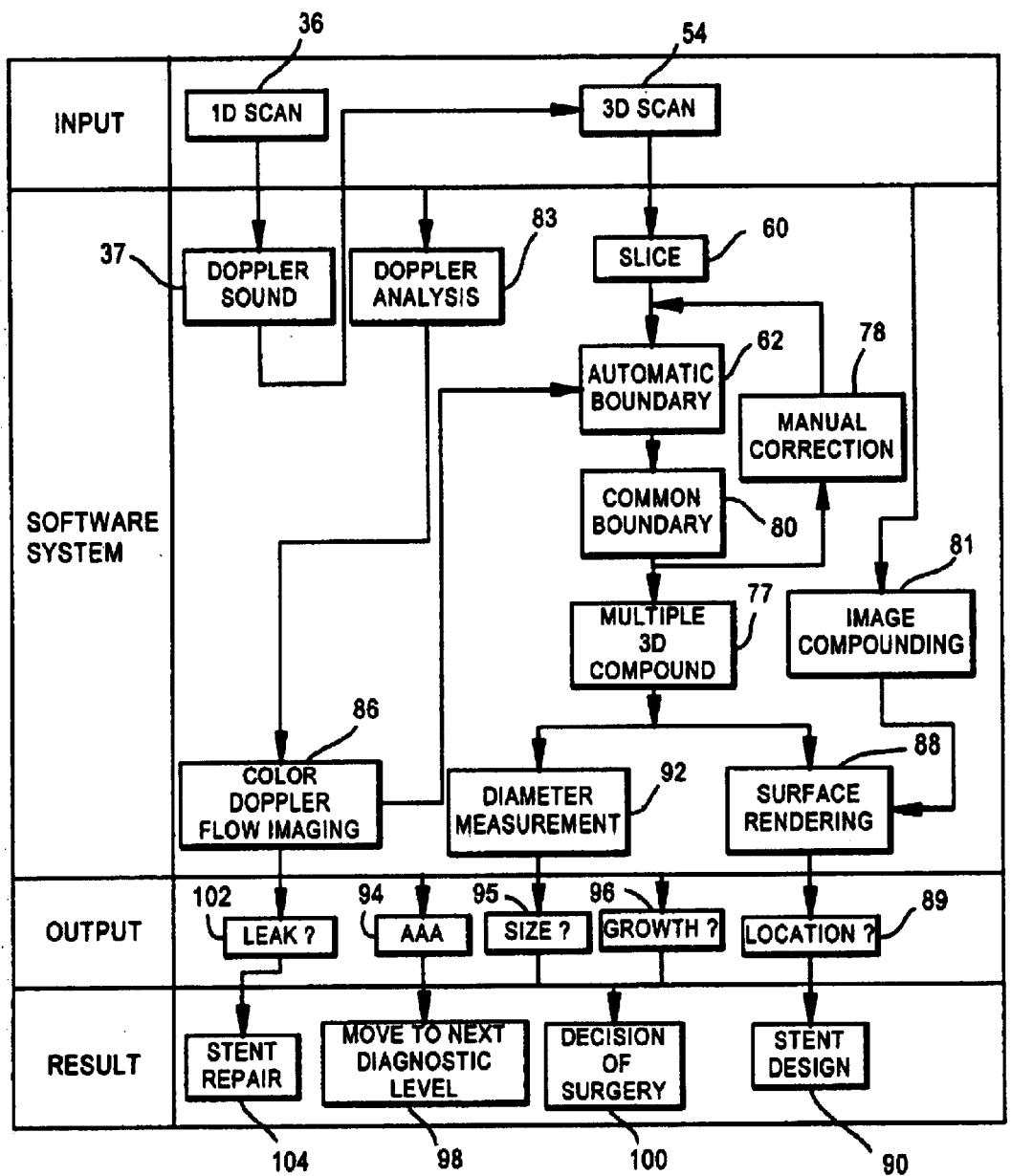
FIGS. 6 and 7 are flow charts showing the function of the system of the present invention, including software portions thereof.

The ultrasound information is then processed, as shown by a portion of the block diagram of FIG. 6. The one-dimensional scan referred to above is shown at block 36. As indicated above, this is a single beam in which the scanhead is in a fixed position. The transducer transmits pulsed ultrasound signals at a single angle of ø and receives the signals back.

Figure 4:
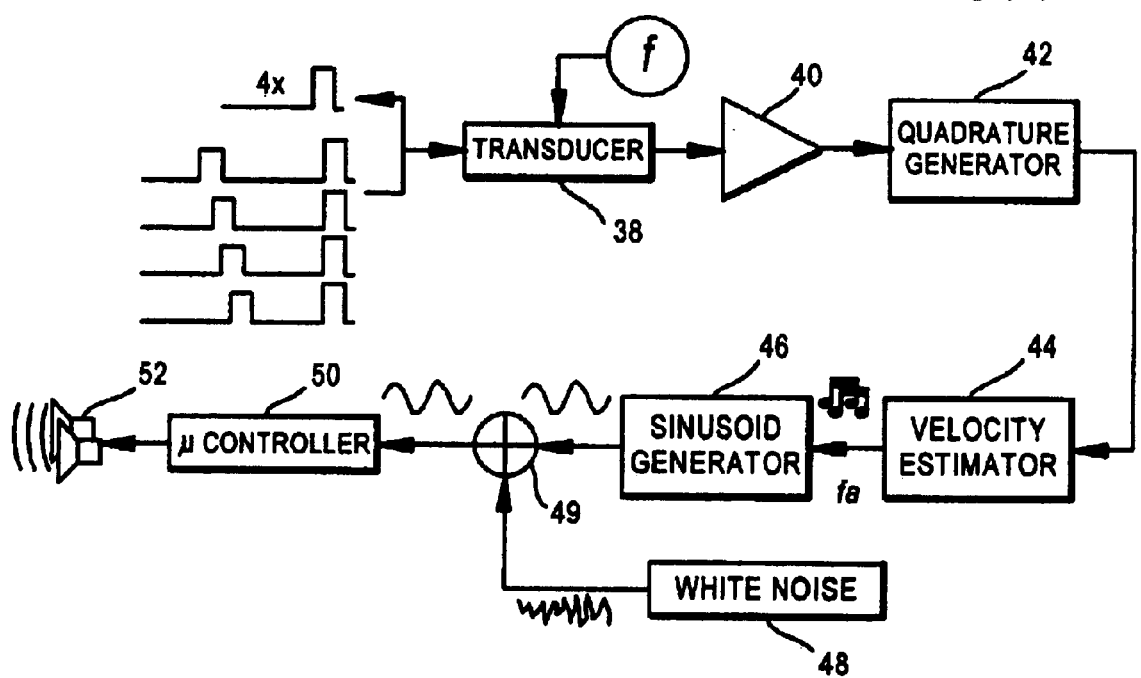
FIG. 4 is a diagram of a portion of the system of the present invention.

FIG. 4 shows the Doppler processing system for sound production. The returning signals 36 from the blood flow are applied through the transducer 38 and then to a TGC gain device 40. The signals from the TGC device are then processed with quadrature pairs at 42; the velocity of the blood flow is then estimated at 44, and a sinusoidal signal corresponding to that velocity is generated by generator 46. The sinusoid produced by generator 46 is monotonic, so white noise from generator 48 is added at 49 to the output from the sinusoidal generator 46, with the resulting signal applied to a microcontroller 50, the output of which is applied to a speaker 52, which produces an audible blood flow sound.

Referring again to FIG. 6, the Doppler blood flow sound (block 37) is used by the operator as discussed above to position the scanner properly to initiate operation of the full three-dimension scan, shown at block 54.

As indicated above, the result of the three-dimensional scan by each transducer is information, in plane coordinates, involving the variables r (depth), ø (scan plane angle) and θ (angle of rotation), as shown in FIGS. 2 and 2A. In the present system, in order to produce a scan of the aorta in three dimensions, the information produced in plane coordinates is converted to spherical coordinates. By converting to spherical coordinates, the scan data comprises a series of data "slices" which are arranged at approximately right angles to the aorta. This is desirable, in that it makes it possible to accurately determine boundary and diameter information. The "slices" of data in spherical coordinates are expressed in four variables, including a range or depth r (similar to plane coordinates), a tilt angle β of the beam within a particular slice, the tilt angle ψ of the entire slice relative to the vertical axis and a rotation angle γ. Any point $P_r$ in the spherical coordinates can be calculated from any point P in the plane coordinates as follows:

$$\beta = \sin^{-1}(\sin \varnothing \cdot \sin(\theta - \gamma))$$

$$\psi = \tan^{-1}(\tan \varnothing \cdot \cos(\theta - \gamma))$$

$$\gamma = \text{arbitrary}$$

lane coordinates the location of each point is defined by three parameters, while in the "slice" spherical coordinates each point is defined by four parameters, the parameters of a point in spherical coordinates, when converted from the plane coordinates, can be determined with γ as a variable. Since γ is an arbitrary value, $P_r$ has a range of potential values for each voxel depending upon γ, i.e. it does not have a unique value for each voxel P in plane coordinates. The spherical coordinate values of a given point can also be converted back to plane coordinates by the following calculations:

$$\varnothing = \cos^{-1}(\cos \beta \cdot \cos \psi)$$

$$\theta = \tan^{-1}\left(\frac{\tan \beta}{\sin \psi}\right) + \gamma$$

Figure 5:
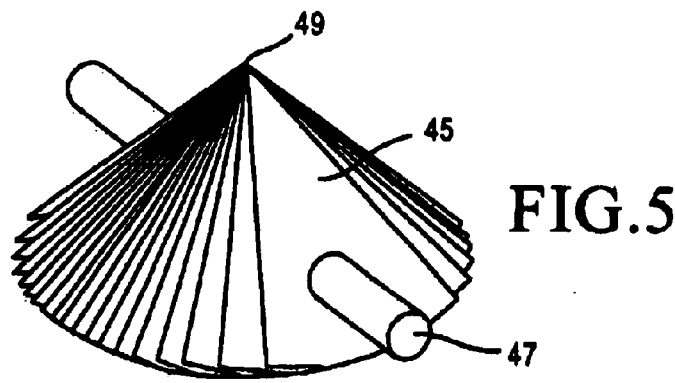
FIG. 5 shows the scan planes as they intersect the aorta after conversion to spherical coordinates.

FIG. 5 shows the revised three-dimensional scan view using the information obtained in plane coordinates after conversion to slice coordinates. Each slice 45 contains a cross-section of the aorta 47 at various tilt angles from a vertex point 49. Each slice is perpendicular (edge to edge) relative to the aorta. The conversion of the ultrasound data from plane coordinates to spherical coordinates is represented by block 60 in FIG. 6. In the next step, the ultrasound information in the slices is used for boundary detection, which is determined automatically and is shown at block 62. The automatic boundary detection process mimics the manner in which a trained sonographer determines the boundary.

Figure 7:
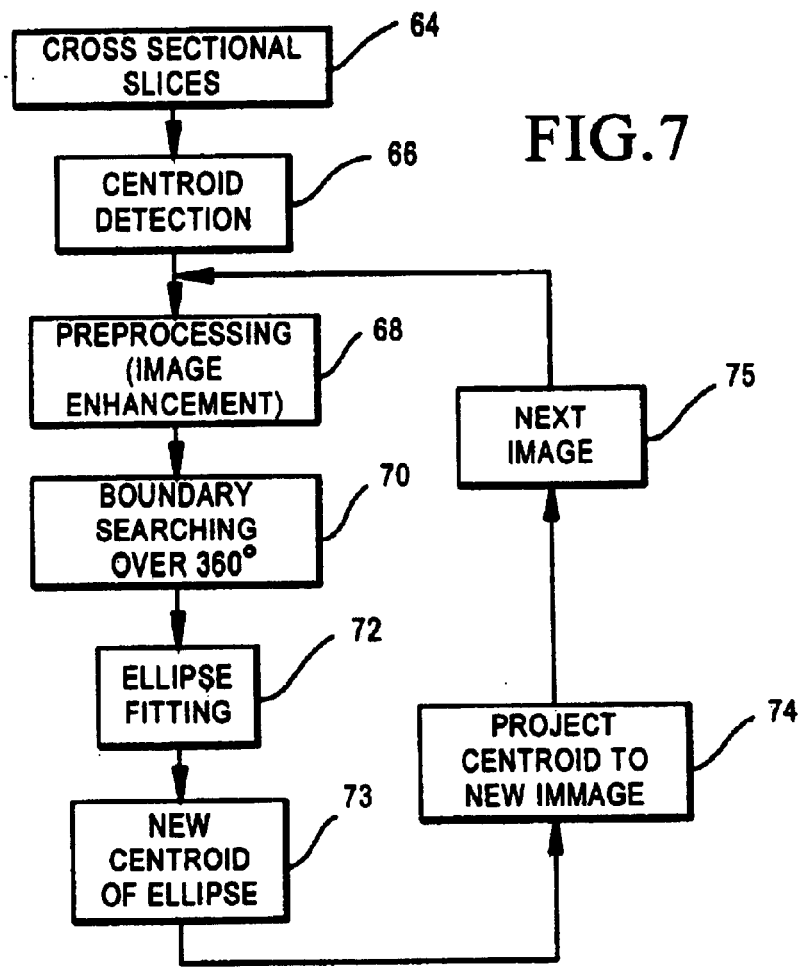

The boundary detection process is shown in FIG. 7. It uses an ellipse fitting approach, based on the fact that the cross-section of the aorta is either a circle or an oval. Using the cross-sectional slices (block 64), starting with the slice having a tilt angle ψ from the vertical of 0°, the center point of the aorta for that slice is determined by moving a square "window" and checking to see if all the pixels within this window are below a certain threshold. The center point is determined (block 66) by averaging those points passed by the block windowing step. A two-dimensional low-pass filter is then used to remove undesired noise (block 68).

From the center point of the first slice outwardly over 360°, the intensity profiles are obtained by resampling, shown at block 70. The inner layer or surface of the aortic wall is the first point whose intensity is above the threshold in the profile when the range from the center point is increased. Ellipse fitting is then approximated to define the aortic wall, shown at block 72. The centroid of the fitted ellipse is determined (block 73), which point is then projected to the next slice (block 74). The next slice is processed in the same way as the first slice, to determine a boundary of the next slice (block 75). This continues until all the slices from the transducer (scanhead) have been processed.

The automatic boundary detection system described above operates in successive ultrasound slices. This information can be verified and corrected from a different viewpoint. For instance, the points of the boundary in slice coordinates can be converted to plane coordinates and then displayed. In the plane images, the boundaries can be verified and corrected; these modified points in plane coordinates can then be converted back to the slice coordinates for reprocessing and correction. This is shown at blocks 77 and 78 in FIG. 6.

Figure 8A:
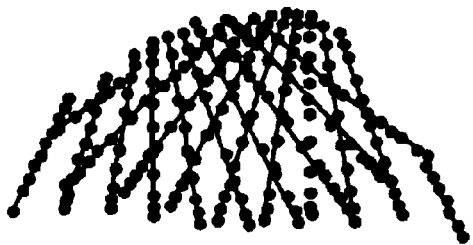
FIGS. 8A–8D are diagrams showing the result of the various steps in the boundary determining portion of the system of the present invention.
Figure 8B:
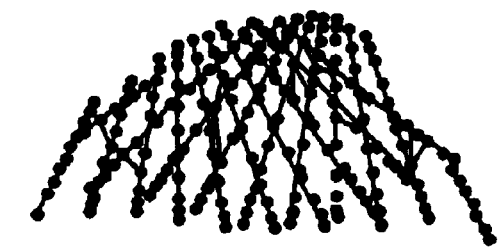
Figure 8C:
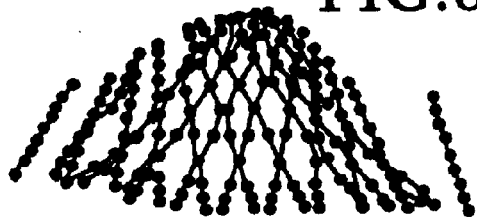
Figure 8D:
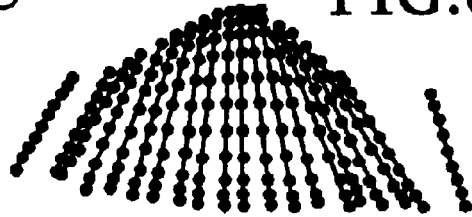

The boundaries of each three-dimensional data set (from the three dimensional scan) can be then compounded in space, i.e. added together, by superimposing all the boundaries using the position and orientation information provided by the multiple scanhead scanning device (DCD). The compounded boundaries of the multiple scanhead images, however, intersect and overlap each other along the aorta. Each boundary will include the same number of points evenly distributed by angle from the origin. The disordered boundaries are sorted and low pass filtered to reject the out of bound ones. Linear regression by resampling is then applied to fit the points in each boundary into a plane. FIGS. 8A–8D show the results of the boundary compounding steps, from superimposition (8A), sorting (8B), low pass filtering (8C) and resampling using linear regression. (8D). The filtered boundary points of FIG. 8C are not in a single plane. With linear regression, the compounded boundaries of FIG. 8D are ready for diameter measurement and surface rendering, as discussed in more detail below.

Figure 9:
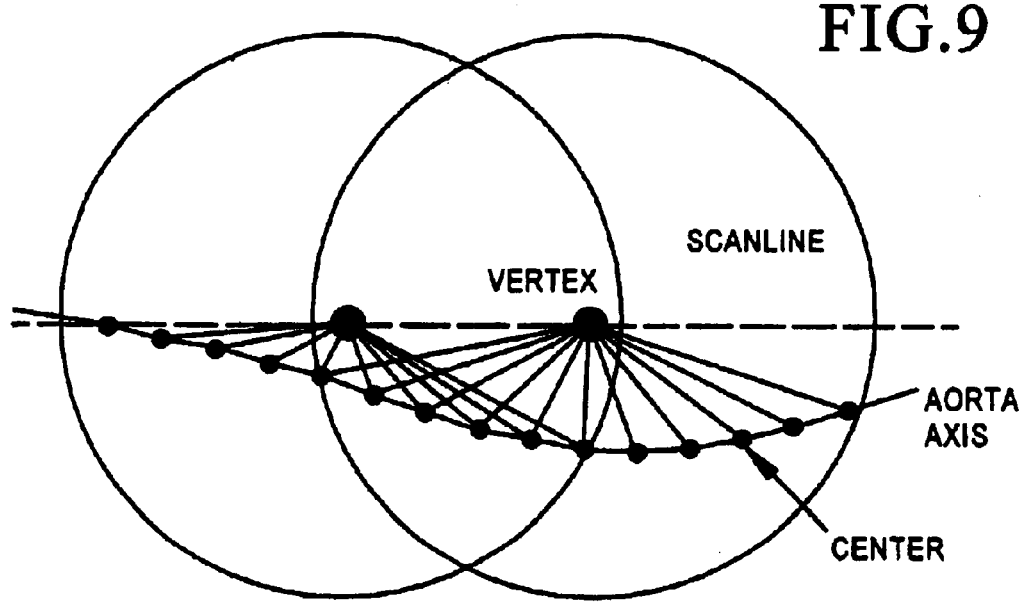
FIG. 9 is a diagram showing the overlapping coverage of the ultrasound scans of the system of the present invention.

The system also uses an image compounding technique as indicated in block 79, from the three-dimensional scan information of multiple scanhead DCD. This extends the image window longitudinally along the aorta, such that the entire longitudinal section will include a normal aorta aneurysm and the iliac bifurcations. The compounding of the image by using multiple scanheads has an advantage, since it reduces shadow patterns produced by each scanhead individually, and permits data that is present in one image but not in another to appear in the compounded image. The axis of the longitudinal view of the aorta is the connection of the center line of the boundaries, with the scan lines passing through this axis from each vertex of the three-dimensional data being collected. Those scan lines that are not in a single plane are then projected onto the plane that includes five vertica of three-dimensional data and then imaged to form the longitudinal view of the aorta. FIG. 9 shows this longitudinal view of compounding.

The results of the image compounding are used for surface rendering described in more detail below.

Figure 10:
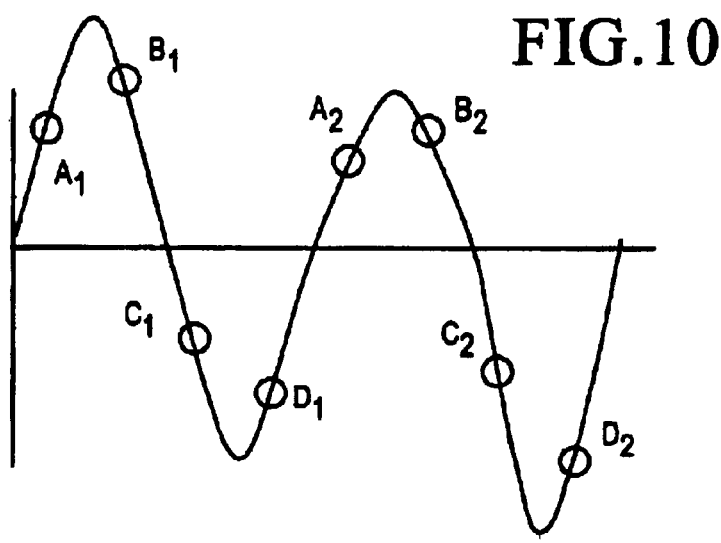
FIG. 10 shows quadrature demodulation using synchronous sampling.

The system also produces a blood flow analysis within the artery via Doppler techniques (block 83). The identification of the aortic wall is important, but the blood flow within the aorta is also important. In the embodiment shown, four consecutive ultrasound waves from the same scanhead are transmitted and the return signals therefrom are sampled synchronously relative to the transmit rate, at a rate of four times the transmit frequency. The quadrature pairs, I (In phase) and Q (Quadrature phase) are computed from the samples according to the following formulas and from FIG. 10:

$$I = \frac{1}{2k} \sum_K (A_K - C_K)$$

$$Q = \frac{1}{2k} \sum_K (B_K - D_K)$$

The quadrature pairs from each ultrasound burst are compared by plotting in the I-Q plane to detect blood flow. Blood flow sound and a colored image can be produced therefrom (block 86).

Referring back to FIG. 6, and in particular the step of surface rendering, a three-dimensional image of the aorta is produced from the image compounding information (block 81) and the multiple three-dimensional compound information (block 77), both discussed above. This surface rendering imaging (block 88) can be accomplished through various well-known methods. This surface information is used to assist in determining the location of the aneurysm and the extent thereof (block 89) and a resulting stent design (block 90).

A diameter measurement (block 92) of the abdominal aortic aneurysm is made from the multiple three-dimensional compound information (block 77). The diameter of the abdominal aorta permits detection and monitoring of an aneurysm. Although there is no currently generally accepted way of diameter measurement, many physicians use a transverse cross-section of the aorta as the diameter. Diameter can also be determined by using the mean length of the center line of the aorta and extending that to the boundary of the aorta over 360°.

The diameter (D) may be calculated using either area or circumference calculations, according to the well-known formulas of:

$$D = 2\sqrt{\frac{area}{\pi}} \quad \text{or} \quad D = \frac{circumference}{\pi}$$

The measurement using a two-dimensional ultrasound instrument in any image plane will produce a real cross-section. The "sliced" image planes of the present system showing the cross-section of the aorta are not all exactly perpendicular to the longitudinal axis of the aorta. The measured diameter from these slices will be somewhat larger than the true cross-sectional diameter.

The largest cross-sectional measurement is usually displayed with the diameter in centimeters. Since the instrument knows the angle of the image relative to the centerline of the aorta, and the centerline of the ultrasound beam, correction for three-dimensional spread of the ultrasound can be made, resulting in an accurate off-axis diameter measurement, as indicated below.

The basic procedural steps of determining the cross-sectional diameter with slices of ultrasound data include first the determination of the center of each slice, as discussed above. These center or centroid points with the same interval on the longitudinal axis are then resampled. An arbitrary plane is tilted for the center point in each plane and the boundary points on each plane are resampled, followed by an estimate of the diameter in the tilt angle direction. The tilt angle with the minimum diameter is then selected and the diameter at that tilt angle is then calculated. The extended diameter measurement (over a length of the aorta) is then shown by plotting the diameters over the desired distance. The diameter measurement is used to determine an aortic aneurysm (block 94), as well as the size thereof (block 95) and whether or not the aneurysm has grown (monitoring function) (block 96). A diagnostic decision can be made (block 98) from block 94 and whether surgery is indicated (block 100) from blocks 95 and 96.

The information from the Doppler flow imaging process (block 86) can be used to determine whether an existing stent is leaking (block 102) and whether or not a stent repair is needed (block 104). The decision and recommendations set forth in blocks 90, 98, 100 and 104 can then be accomplished by a physician reviewing the medical output information provided. The system itself can be used for recommendations, based on comparing the output information against preset threshold values.

Hence, in the present invention, a system for determining and monitoring an abdominal aortic aneurysm is disclosed, involving an ultrasound scan and processing of that information to produce boundary and diameter information of the aorta over a selected length thereof, leading to a determination of the aneurysm and a change therein, if any, since the last scan. Other aspects of the system include use of Doppler analysis relative to blood flow to determine whether a previously positioned stent is leaking.

Surface rendering of the aorta also can be provided to assist in location of the aneurysm along the aorta and the stent design. This surface rendering is significant, since it makes it easier for the physician to discuss treatment options and for the patient to understand visually the extent and significance of the medical condition.

Also, since the web server incorporates a database, a record can be maintained of the patient's aortic condition over time. The progression of the condition can then be accurately monitored, leading to better treatment decisions. Using the surface rendered information, the progression of the disease can be seen visually over time, somewhat like a video of the organ over time.

Although a preferred embodiment of the invention has been disclosed here for purposes of illustration, it should be understood that various changes, modifications and substitutions may be incorporated in the embodiment without departing from the spirit of the invention, which is defined by the claims which follow.

What is claimed is:

1. A system for abdominal aortic aneurysm evaluation and monitoring, comprising:
   a hand-held data collection device which includes a plurality of separate ultrasound sources for obtaining three-dimensional ultrasound scan information of a selected portion of an abdominal aorta, each ultrasound source producing a three-dimensional scan, comprising a plurality of scan line planes, the three-dimensional scans arranged so as to overlap each other along the selected portion of the aorta;
   a processor for converting the scan line plane information obtained by the plurality of ultrasound sources to coordinates in which the converted scan line planes slice approximately perpendicularly through the aorta;
   a processor for determining aorta boundary information from the converted scan information; and
   a calculation circuit for calculating the diameter of the aorta from the boundary information, wherein diameter information of the aorta at a plurality of locations therealong is useful in determining the existence of an aneurysm in the abdominal aorta artery.

2. A system of claim 1, wherein the data collection device is initially positioned with an ultrasound beam in one dimension, wherein the system further includes a Doppler processing system for producing an audible sound when the data collection device is positioned over the aorta, thereby assisting the operator in initially positioning the data collection device on the patient.

3. A system of claim 2, wherein the Doppler processing system operates to provide an image of blood flow through the aorta, which is useful in determining whether an existing stent in the aorta is leaking.

4. A system of claim 1, wherein the converted scan planes slice through the aorta, separated by a preselected tilt angle relative to a vertex point of a source of the ultrasound signals.

5. A system of claim 1, wherein the boundary information is provided by an ellipse fitting process using first a scan plane having a tilt angle of 0°, followed by the remaining scan planes to produce a center line of the aorta and a location of the boundaries of the aorta outwardly from the center line.

6. A system of claim 5, wherein the calculating circuit operates to produce a diameter indication of the aorta, and wherein the diameter indication is made for a plurality of points along the aorta, so that an aneurysm in the aorta can be identified and monitored.

7. A system of claim 1, wherein the boundary information is compounded by the processor to produce a visual representation of the surface of the aorta.

8. A system of claim 7, wherein the three-dimensional image has a surface rendering aspect which provides a realistic representation of the aorta.

9. A system of claim 1, including a database in which is stored results of successive scans, so that progression of the condition can be determined over time.

10. A method for abdominal aortic aneurysm evaluation and monitoring, comprising the steps of:
    obtaining three-dimensional ultrasound scan information of a selected portion of an abdominal aorta from a plurality of ultrasound sources, each ultrasound source producing a three-dimensional scan, the three-dimensional scans arranged so as to overlap each other along the selected portion of the aorta;
    converting the scan line plane information obtained by the plurality of ultrasound sources to coordinates in which the converted scan line planes slice approximately perpendicularly through the aorta;
    determining aorta boundary information from the converted scan information; and
    calculating the diameter of the aorta from the boundary information, wherein diameter information of the aorta at a plurality of locations therealong is useful in determining the existence of an aneurysm in the abdominal aorta artery.

11. A method of claim 10, wherein the step of obtaining three-dimensional ultrasound scan information is accomplished by a data collection device which is initially positioned using an ultrasound beam in one dimension, wherein the system includes the further step of producing an audible sound when the data collection device is positioned over the aorta, thereby assisting the operator in initially positioning the data collection device on the patient.

12. A method of claim 10, including the step of providing an image of blood flow through the aorta, which is useful in determining whether an existing stent in the aorta is leaking.

13. A method of claim 10, wherein the converted scan planes slice through the aorta separated by a preselected angle relative to a vertex point from a source of ultrasound signals.

14. A method of claim 10, wherein the step of determining the boundary information includes the use of an ellipse fitting process, using first a scan plane having a tilt angle of 0°, followed by the remaining scan line planes, to produce a center line of the aorta and then a location of the boundaries of the aorta outwardly from said center line.

15. A method of claim 10, including the step of compounding the boundary information to produce a visual representation of the surface of the aorta, wherein the boundary information is rendered so that it is a realistic representation of the aorta.

16. A method of claim 10, including the step of storing the results of successive ultrasound scans so that progression of the condition of the aorta can be determined over time.

* * * * *